United States Patent [19]
Kassel

[11] Patent Number: 5,114,341
[45] Date of Patent: * May 19, 1992

[54] DENTAL MATRIX

[76] Inventor: Larry I. Kassel, 1347 Hickory Hollow Dr., Flint, Mich. 48532

[*] Notice: The portion of the term of this patent subsequent to Mar. 5, 2008 has been disclaimed.

[21] Appl. No.: 642,030

[22] Filed: Jan. 16, 1991

Related U.S. Application Data

[63] Continuation-in-part of Ser. No. 351,386, May 15, 1989, Pat. No. 4,997,367.

[51] Int. Cl.⁵ ............................................... A61C 5/04
[52] U.S. Cl. ..................................................... 433/39
[58] Field of Search ..................... 433/39, 40, 218, 226

[56] References Cited

U.S. PATENT DOCUMENTS

| | | | |
|---|---|---|---|
| 1,379,489 | 5/1921 | Taylor | 433/39 |
| 2,310,448 | 2/1943 | Leib | 433/39 |
| 2,611,182 | 9/1952 | Tofflemire | 433/39 |
| 2,674,801 | 4/1954 | Trangmar | 433/39 |
| 3,842,505 | 10/1974 | eames | 433/39 |
| 4,718,849 | 1/1988 | von Weissenfluh et al. | 433/39 |

Primary Examiner—Cary E. O'Connor
Attorney, Agent, or Firm—Gifford, Groh, Sprinkle, Patmore and Anderson

[57] ABSTRACT

A method and apparatus for use in restoration procedures for teeth. The apparatus includes a matrix having a form portion extending between a pair of wings. The form portion has an anatomically contoured inner surface which extends between a pair of corners. The wings of the matrix are affixed together by an adhesive strip. A tapered flange extends outwardly from the form portion for insertion between the gingiva and tooth to permit introduction of restorative material in the gingival and/or subgingival area. The matrix is formed of clear material to permit viewing of the restorative material during the procedure.

13 Claims, 3 Drawing Sheets

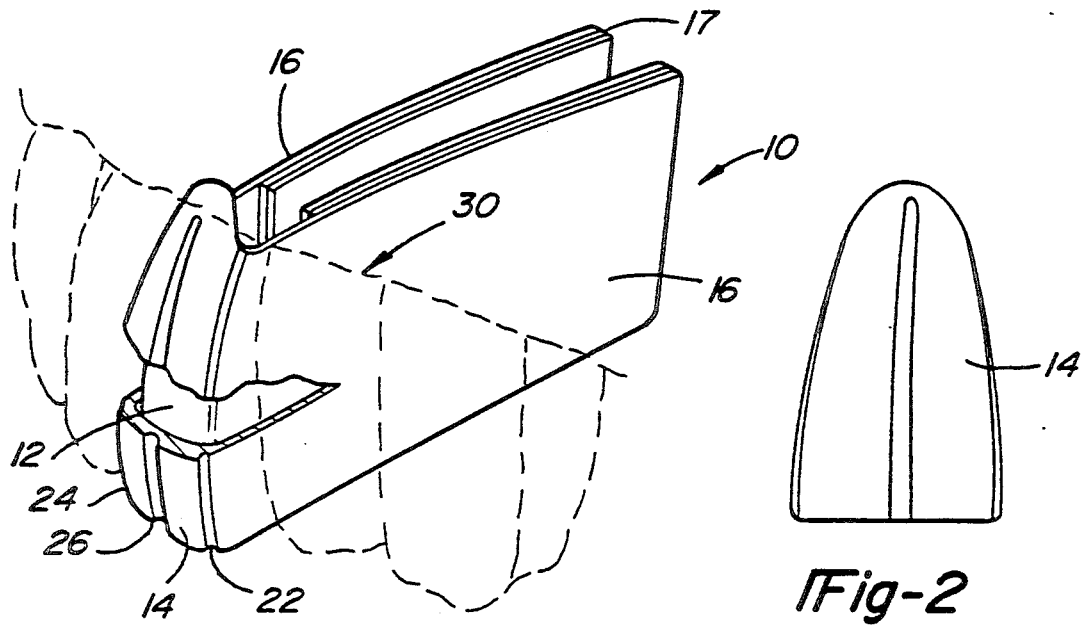
Fig-1
Fig-2
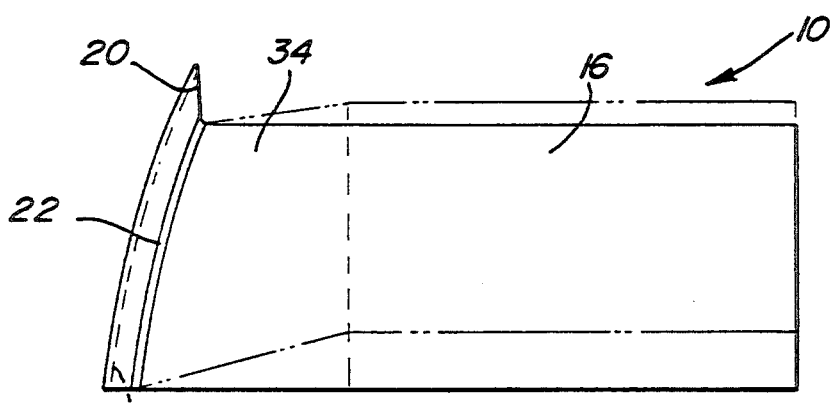
Fig-3
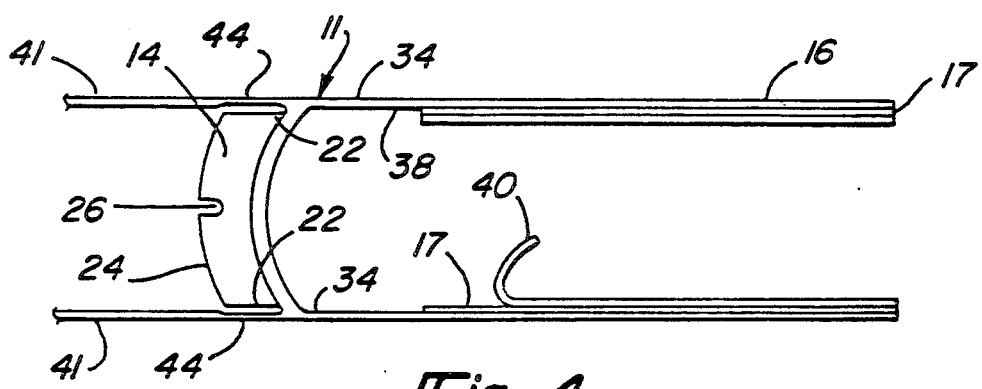
Fig-4

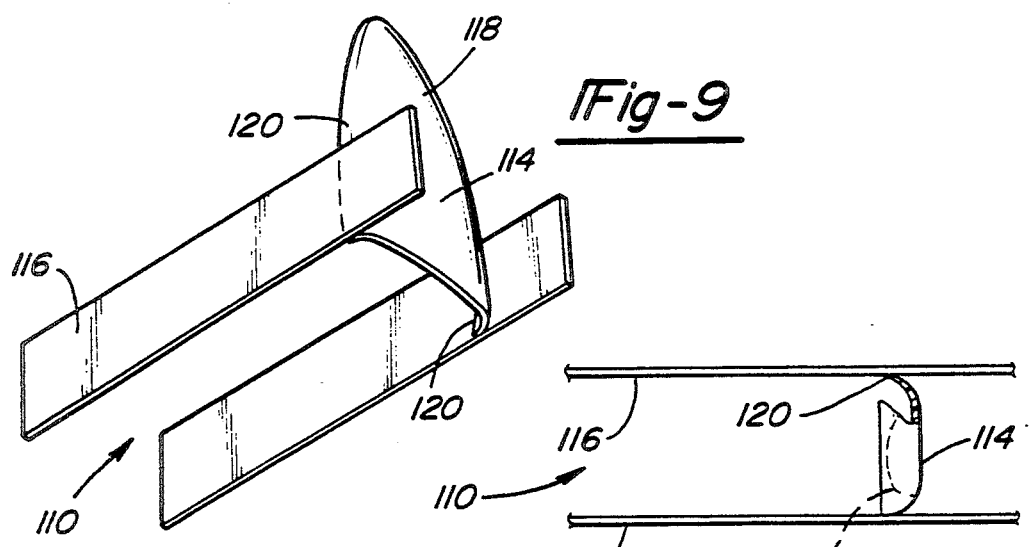
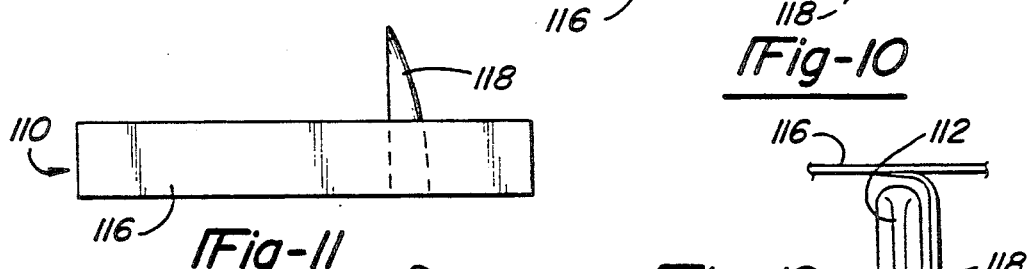
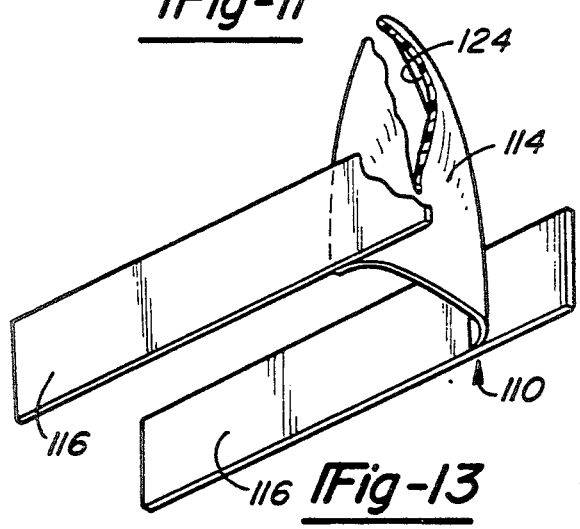
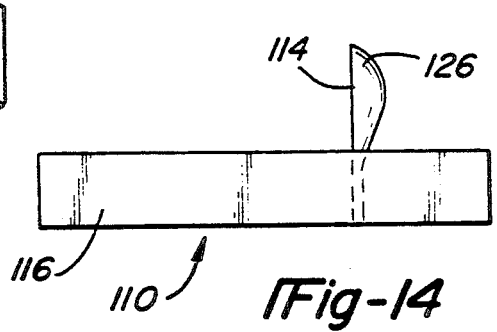
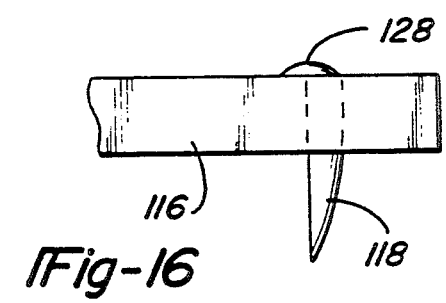
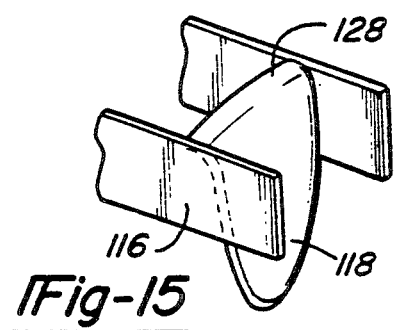

DENTAL MATRIX

This is a continuation-in-part of copending application Ser. No. 07/351,386 filed on May 15, 1989 now U.S. Pat. No. 4,997,367.

BACKGROUND OF THE INVENTION

I. Field of the Invention

The present invention relates to a dental matrix, and more particularly to a dental matrix for use in restoration of a tooth.

II. Description of the Prior Art

The application of a restorative material to a patient's tooth for cosmetic and curative purposes is known. Typical methods of applying restorative material are, cementing prefabricated veneers to a surface of the tooth, bonding veneers or coatings of composite material to a surface of the tooth or filling voids or cavities with restorative material and the like.

Veneers or coatings of composite restorative may be applied for reconstructing teeth or for restoring or masking defects such as developmental abnormalities and fluorosis stains.

The surface of a damaged tooth may be restored by applying a composite restorative resin such as Heliosit or Silux to the surface and curing the material. In order to maintain proper spacing between the tooth being restored and adjacent teeth, the dentist may insert a Mylar strip encircling the tooth and restorative resin during the curing step.

A decayed portion of a tooth may be restored by mounting a celluloid crown form to a tooth and injecting restorative material into the cavity or void. However, such crown forms are frequently too thick to be positioned interproximally to maintain proper spacing. After the restorative resin is cured, the dentist contours, shapes, and polishes the restorative material so as to produce an appearance of a properly formed and colored natural tooth. However, considerable skill and time on the part of the dentist is required to produce a proper form and an attractive appearance to the coating of the restorative material. Additionally, it is difficult to control and observe the restorative material within the crown form resulting in undesired voids in the restorative material after curing.

It is also known to form a prefabricated veneer of porcelain or composite material over a dental cast or model for bonding to the surface of a tooth. As is disclosed in U.S. Pat. No. 4,226,593 to Cohen et al, a veneer blank is ground and shaped by a lab technician using a dental cast of the patient's teeth. The veneers are then encompassed by a flexible mold for removal from the dental cast and transferred in proper orientation to be secured on the patient's teeth. However, this method requires preparation of special molds and dental casts. As a result, this method is quite time consuming and costly.

Thus, it would be desirable to have a method and apparatus which would greatly reduce the amount of time, skill, and expense of applying coverings such as restorative materials and veneers to teeth.

SUMMARY OF THE INVENTION

The present invention thus provides a method and apparatus for the application of restorative material to damaged, decayed, or abnormally formed teeth. The apparatus includes a matrix having a form portion extending between a pair of wings. The form portion has an inner surface which is anatomically contoured to form a desired surface shape on a portion of a tooth requiring restoration. The anatomically contoured inner surface is positioned adjacent the surface of the tooth to be repaired by the pair of wings. The wings extend interproximally and may be fastened about the tooth by adhesive strips affixed to at least one of the pair of wings. The matrix, so positioned, provides a mold for restorative material. The inner surface may be formed for repairing the lingual, incisal, interproximal and/or labial surfaces of the tooth. The matrix may be used during the installation of a preformed veneer on the tooth to isolate the tooth during preparation and etching steps as well as maintaining the proper interproximal spacing and exert pressure to hold the veneer during bonding.

A tapered flange extends outwardly to permit insertion of the inner surface of the matrix subgingivally and thereby permit adaptation of restorative material at the gingival and/or subgingival aspect of the tooth.

The matrix is formed of a clear material to allow for the use of light curing material and for observation of the restorative material. The matrix, thus, may be used as a form for shaping the restorative material, thereby resulting in a proper contour, requiring less skill of the part of the dentist to perform the shaping, and drastically reducing the finishing and polishing time. The matrix may be used during the bonding of restorative material in the repair of decayed teeth. The device permits proper interproximal spacing and gingival and/or subgingival adaptation of restorative material.

The present invention is primarily for use in composite resin bonding procedures. It is designed to aid the dentist or technician in accomplishing this procedure more quickly, accurately, and with more consistent results. It has been found that force transmitted to the bonding material by pulling on the wings of the matrix condenses and imparts energy to the restorative material. This additional energy results in an improved bonding of the restorative material to the surface of the tooth, enhances the strength of the restorative material and improves the resistance of the restorative material to staining. Bonding with the matrix requires less finishing, trimming, and polishing time of the restoration. It also allows multiple teeth to be bonded simultaneously, while still allowing for proper interproximal contour and spacing. The present invention also allows for the matrix to be held in place about the tooth by itself thereby freeing the hands of the dentist.

BRIEF DESCRIPTION OF THE DRAWING

A better understanding of the present invention will be had upon reference to the following detailed description, when read in conjunction with the accompanying drawing, wherein like reference characters refer to like parts throughout the several views in which:

FIG. 1 is a perspective view of the device in position on a tooth according to the invention;

FIG. 2 is a front view of the matrix according to the invention;

FIG. 3 is a side view of the matrix according to the invention;

FIG. 4 is a top view of a first alternative embodiment of the matrix according to the invention;

FIG. 9 is a perspective view of a fourth alternative embodiment of the invention in which the matrix is formed of three separate pieces which are electronically welded together;

FIG. 10 is a bottom view of a fourth alternative embodiment of the matrix according to the invention;

FIG. 11 is a side view of the fourth alternative embodiment of the matrix according to the invention;

FIG. 12 is a fragmentary bottom view of the fourth alternative embodiment of the matrix about a tooth;

FIG. 13 is a perspective view of a fifth alternative embodiment of the matrix according to the invention;

FIG. 14 is a side view of the fifth alternative embodiment of the invention;

FIG. 15 is a perspective view of a sixth alternative embodiment of the matrix according to the invention; and FIG. 16 is a side view of the sixth alternative embodiment of the invention.

DETAILED DESCRIPTION OF THE PREFERRED EMBODIMENT

Figure 5:
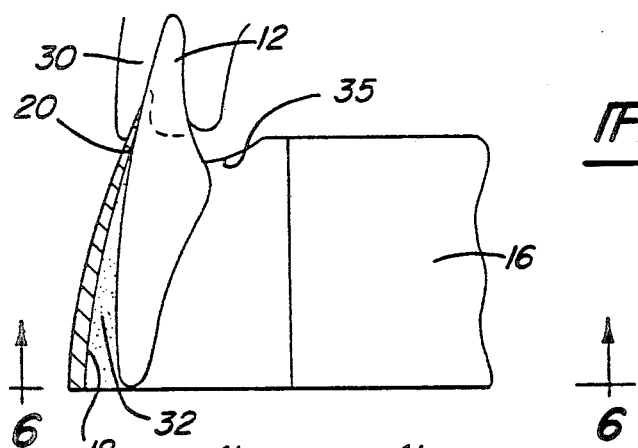
FIG. 5 is a cross-sectional view of the matrix along lines 6—6.

As best shown in FIG. 1, an apparatus, such as a matrix 10, is shown for restoration of a tooth 12. The matrix 10 has a form portion 14 extending between a pair of wings 16. Each of the pair of wings 16 has an adhesive material 17 on an inner surface 18 for attaching the pair of wings 16 together to secure the matrix to the tooth 12, as set forth below and best shown in FIG. 6. The matrix is formed of a suitable clear moldable material such as a polyester film. The clear material permits curing of photosensitive compounds by visible light. As set forth below, the wings are formed with a thin cross section and are flexible. The form portion 14 has a thicker cross section than the wings in order to resist deformation.

Figure 6:
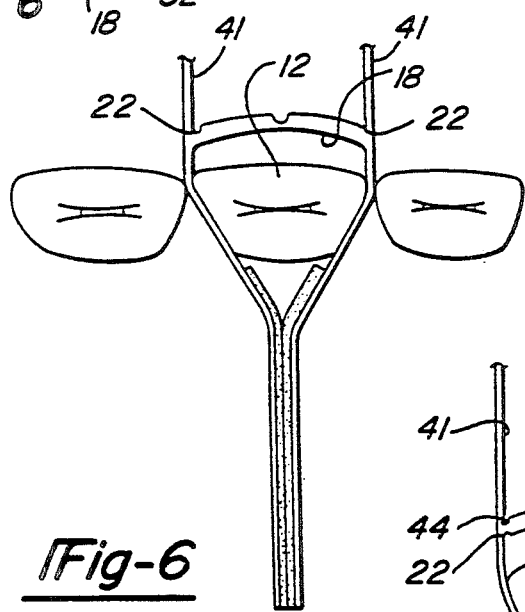
FIG. 6 is a bottom view of the first alternative embodiment of the matrix about a tooth.

The form portion 14 of the matrix has a contoured inner surface 18 and tapered flange 20. As shown in FIG. 6, the inner surface 18 extends between a pair of corner grooves 22 formed between the form portion and the pair of wings 16. The inner surface 18 is anatomically contoured to have a surface complementary to a desired labial surface which is to be formed on the tooth. The inner surface 18 is formed to provide a mold for composite restoration material 32 as shown in FIG. 5. Because of the variety of sizes and shapes of human teeth, a number of matrices having different sized and shaped inner surfaces will be formed to properly accommodate differed sized and shaped teeth. The matrix will be formed in a suitable manner, such as molding, to provide an inner surface having a specific, predetermined anatomical contour and size.

The form portion 14 has a thickness sufficient to maintain the predetermined anatomical contour of the inner surface 18 when the wings 16 are affixed together. The form portion 14 is provided with an outer surface 24 which may be provided with a center groove 26, as shown in FIGS. 1 and 2. The center groove 26 extends vertically on the outer surface corresponding generally with the width "W" of the pair of wings so as not to extend on the flange 20 to irritate gingival tissue 30. The center groove 26 thus formed permits the form portion to bend slightly along the groove when the wings are pulled and secured tightly against the lingual surface of the tooth 12. In this manner, the radius of curvature of the inner surface 18 can be altered to narrow the distance between the pair of corner grooves 22 if the inner surface is wider than desired to be formed on the tooth, as is discussed more fully below. The pair of corner grooves 22 are formed at the juncture of each wing and the form portion of the matrix 10 to permit the wings to flexibly bend as desired to permit the wings to extend along the proximal surfaces of the tooth at the desired angle. Any excess restorative material is forced midfacially and extruded incisially from the matrix, resulting in a minimal amount of finishing necessary.

The tapered flange 20 extends outwardly beyond the pair of wings 16 for insertion under the gingival tissue 30 as shown in FIG. 1 and FIG. 5. The tapered flange 20 permits proper adaptation of restorative material 32, at the gingival or subgingival aspect of the tooth, as shown in FIG. 5.

Each of the pair of wings 16 extends outwardly from one of the corner grooves 22 of the matrix, as best shown in FIG. 4. The corner grooves 22 permit ready movement of the wings with respect to the facial surface. Each wing has an intermediate portion 34 extending between one of the corners 22 and a free end 36 having the adhesive pad 17 on an inner surface 38. Each intermediate portion 34 has a thin cross section to permit interproximal insertion of the wings. Each wing is sufficiently flexible to conform to the contour of the proximal and labial surfaces of the tooth 12. If matrices are used on adjacent teeth at the same time, each wing must be sufficiently thin to permit two wings to pass interproximally. The intermediate portion 34 has a width and length generally equivalent or less than the proximal surface of the tooth.

A notch 35 may be formed, as shown in FIG. 5, for accepting the gingiva. Additionally, the intermediate portion 30 and the free end may be angled with respect to each other and to the form portion to permit proper alignment, as shown in phantom on FIG. 3.

Extending along the inner surface of each of the pair of wings from the lingual surface is the adhesive material 17 as shown in FIG. 1. The adhesive material 17 may be any suitable type which permits adhesion on contact, and in the preferred embodiment, is a strip of resilient material having adhesive on both sides. A sheet 40 of protective material, such as waxed paper, extends along the outer surface of the strip to prevent inadvertent adhesion of the wings. The sheet 40 of protective material is removed prior to final positioning of the matrix about the tooth.

Figure 8:
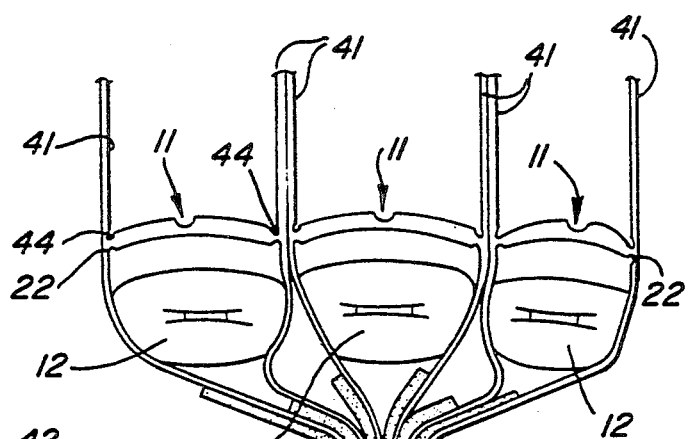
FIG. 8 is a bottom view of three matrices according to the first alternative embodiment of the invention which have been coupled together.

A first alternative embodiment is of a matrix 11 shown in FIGS. 4, 6 and 8. The matrix 11 is formed similarly to matrix 10, but additionally includes a pair of arms 41 extending outwardly from the outer surface 24. The pair of arms 41 extend from corner grooves 44 for grasping by the dentist or technician to facilitate the positioning of the matrix 11.

Figure 7:
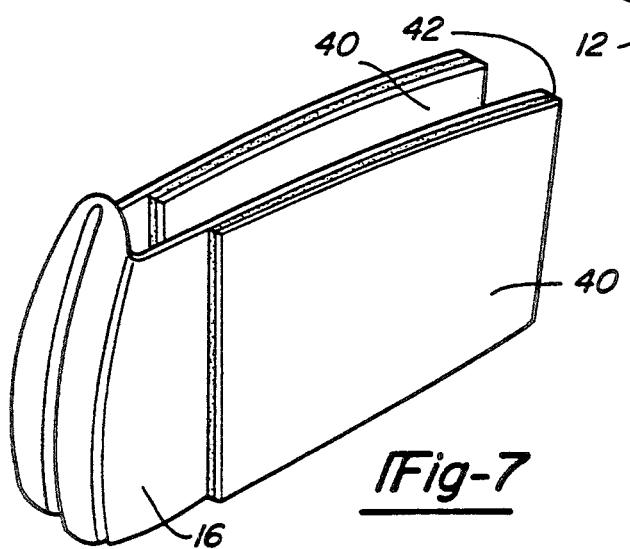
FIG. 7 is a perspective view of a second alternative embodiment of the matrix according to the invention.

As shown in FIGS. 7 and 8, an exterior adhesive strip 42 may be positioned on an outer surface of the wing to permit joining of adjacent matrices when several teeth are being restored. The wings and form portion of the matrix may be formed of the same material in a unitary molding process, or may be formed of separate pieces as shown in FIG. 9 and discussed below.

In accordance with the invention, other surfaces of the tooth besides the facial or labial surface may be restored by utilizing appropriately shaped anatomical forms. A matrix 110 according to the invention is suitable for use in restoring facial and interproximal surfaces is shown in FIGS. 10, 11 and 12. The matrix has form portion 114 extending between a pair of wings 116. The form portion 114 has an inner surface with an anatomically shaped facial section 118 extending between an interproximal section 120.

The matrix may be molded as one piece or in the preferred embodiment the wings 116 and facial portion are molded separately and are joined together by a suitable method such as ultrasonic welding. The thickness of the wings and form portion of the matrix maybe controlled such that it is unnecessary to use grooves and the like as set forth above to determine the proper bending of the wings. The interproximal sections are formed with the desired anatomical interproximal shape. In this way, it is possible to repair the portion of the tooth 112 requiring restoration. The matrix shown in FIGS. 10-12 may be used for repairing either the facial or interproximal inner surfaces separately or together at the same time.

A matrix suitable for use in restoration of a lingual surface of a tooth is shown in FIGS. 13 and 14. The matrix is formed in the same manner as set forth above, however, the form 114 is provided with an inner surface lingual portion 124 having the shape of a desired lingual surface of the tooth. The form portion may be extended with interproximal sections to repair desired inner proximal surfaces.

Finally, as shown in FIGS. 15 and 16, the matrix may be formed for restoration of an incisal surface of a tooth. As shown in FIG. 15, the anatomical form 114 has an incisal portion 128 extending transversely across between the wings 116 and generally normal to the facial portion 118 of the matrix. In the same manner as set forth above, the form portion has an inner surface which is formed to present the desired incisal surface for the tooth to be restored. In this manner, the corner and edges of the incisal, labial or lingual surfaces may be repaired, as well as the surfaces themselves or any combination of surfaces.

Method of Use

I. Use of the restorative apparatus in conjunction with composite resin restorative material and the like.

To repair deformed, decayed, or damaged teeth, the dentist or technician first selects a matrix having an inner surface 18 corresponding to a labial surface or a desired surface to be formed on the tooth.

The matrix 10 is then positioned with the wings extending proximally and the wedge shaped flange is inserted subgingivally. In the case of the alternative embodiment, the matrix 11 is positioned by grasping one arm and its corresponding wing and manipulating the wing interproximally, then the other arm and its corresponding wing are manipulated into its controlateral interproximal position. Once positioned, the wings of the matrix may be pulled and the matrix is then inspected to determine if any trimming of the matrix is necessary. If no trimming is necessary, the matrix may be pulled labially, so that it fits loosely about the tooth with the flange inserted subgingivally. It is placed in this manner in order to allow room for the introduction and manipulation of any etching, bonding and restorative material to be applied. If trimming is necessary, the matrix is removed from the tooth, trimmed, and then reinserted loosely about the tooth with the flange inserted subgingivally. In the case of the alternative embodiment, the arms 41 of the matrix 11 may be cut off once the matrix is in place about the tooth. The etchant, bonding and restorative material are applied in a manner suitable for the particular compounds that the dentist or technician desires to use. After the restorative material is applied, the wings are pulled tightly and affixed. The wings may be affixed symmetrically as shown in FIG. 6, or offset, as shown in FIG. 8. One or both wings may extend along the lingual to permit restoration of a proximal and/or lingual surface of the tooth. The protective sheet 40 is removed from the adhesive strip. The pair of wings 16 are properly positioned and then pressed together to hold the inner surface to a proper position adjacent to the lingual surface of the tooth as shown in FIG. 6. By affixing the adhesive surfaces together, the matrix is maintained on the tooth, thereby freeing the hands of the dentist or technician for other uses. Additionally, wings of adjacent matrices may be affixed one to another so that multiple teeth can be restored simultaneously, as shown in FIG. 8.

When the wings are pulled tightly, the inner surface 18 of the matrix draws closer to the labial surface of the tooth which causes the restorative material which is trapped between the inner portion of the matrix and the tooth to be molded to the proper shape as determined by the selection of the proper sized matrix. Any excess restorative material is extruded incisally out of this pocket formed by the inner surface of the matrix and the tooth, where it Can be easily removed before the restorative material is cured.

The degree of tightness to which the wings are pulled influences the thickness of restorative material that will remain on the labial surface of the tooth. If the dentist or technician desires a thinner amount of material to remain on the labial, he/she simply pulls the wings tighter, causing more of the restorative material to be extruded incisally. The shape of the inner surface 18 of the matrix automatically allows for the restorative material to be thinner at the gingival aspect of the tooth, thereby significantly reducing the risk of the restoration causing gingival irritation.

Because most tooth colored restorative materials have a thixotropic filler phase, the restorative material flows better under pressure. It has been found that the restorative material is compressed and energy is imparted to the restorative material when the wings are pulled. The energy imparted to the material results in a greater strength of the restoration, a more uniform atomic structure, a restoration which is more resistant to fractures, wear and stains. The improved flow of the material results in improved bonding between the tooth and the restorative material. These effects have been confirmed by electron microscope. As a result, use of the matrix results in a more effective bonding process as well as a more efficient and aesthetically pleasing procedure.

When the wings are drawn tightly about the tooth on a matrix having an inner surface 18 of the form portion 14 which is larger than the labial surface or desired surface of a tooth, (see below) then the excess restorative material is extruded incisally and is directed midfacially as the center groove 26 will permit the form portion of the matrix to flex outwardly from the tooth along this groove. After the restorative material is cured and the matrix is removed, this excess material at the midfacial can be easily and quickly trimmed and polished. The center groove 26 ends at a predetermined distance above the gingival so that excess material is not directed at the gingival aspect of the restoration.

When selecting the proper sized matrix to be used, if a matrix having an inner surface 18 corresponding to a labial surface or a desired surface to be formed on the tooth cannot be found, then a matrix having an inner surface 18 slightly larger mesidoistally than the labial surface or a desired surface to be formed on a tooth should be used. When the wings are drawn tightly about the tooth, the form portion of the slightly larger matrix will bend at the center groove 26 resulting in a narrower distance between the pair of corners 22 and will produce a proper fit to the labial surface or the desired surface. Additionally, the corner grooves 22 will allow the form portion of the matrix to flex without disturbing the intermediate interproximal portions of the matrix 34 allowing for these portions to still be maintained about the tooth at the proper angulation. After the wings are pulled and the matrix is positioned properly, the restorative material can be cured. Most of the restorative materials currently in use are light cured. The matrix is translucent and will permit visible and ultraviolet light to pass through the matrix to allow for the curing of photosensitive material. Also, because the matrix is translucent, the restorative material can be viewed to ensure that no voids exist. After the restorative material has cured, the matrix is removed. If necessary, a final forming and shaping of the restorative material may be required. However, the bonding of composite material is accomplished much more quickly than by previously known methods. Also, this method requires significantly less shaping, finishing, and polishing time than prior methods and provides more proper contour of the restorative material, including the contour of the interproximal areas. Also, this method allows an easy way to treat multiple teeth simultaneously and effectively.

II. Use of the restorative apparatus in conjunction with preformed veneers.

The matrix is selected and positioned about the tooth loosely with the flange inserted subgingivally before the etching and bonding in place of the veneer. The matrix will provide for isolation of the tooth during these procedures. The matrix will prevent saliva, water and other unwanted fluids from contaminating the surface of the tooth, and it will prevent etchant solution$ and bonding agents from flowing out of the confines of the matrix and onto the gingiva and adjacent teeth. It will also provide for the proper interproximal spacing between teeth, as it will not allow the bonding agent or cement to flow interproximally between adjacent teeth. Additionally, it will allow for the isolation of multiple teeth so that veneers can be bonded into place on many teeth in less time than present methods allow. Also, because the wings of the matrices adhere to each other as shown in FIG. 6, or one to another, as shown in FIG. 8, the dentist or technician's hands are freed to accomplish other tasks, such as preparation and placement of bonding agents onto the inner surfaces of the veneers.

Having thus described my invention, many modifications thereto will become apparent to those skilled in the art to which it pertains without deviation from the spirit of the present invention as defined by the scope of the appended claims.

I claim:

1. An apparatus for use during restoration Of a tooth having a labial surface, a pair of proximal surfaces, an incisal surface, and a lingual surface, said apparatus comprising:
   a matrix having a form portion, said form portion having an anatomically shaped inner surface adjacent to and covering at least one desired surface of said tooth; and means for pulling said inner surface of said matrix into a position adjacent said desired surface, said means for pulling further comprising at least one interproximal wing attached to and extending from said form portion.

2. The apparatus of claim 1, wherein said means for pulling comprises a pair of wings extending from said form portion.

3. The apparatus of claim 2, wherein said means for pulling comprises at least one adhesive strip mounted to an inner surface of at least one of said pair of wings.

4. The apparatus of claim 1 further comprising means for joining a wing of one matrix to one wing of an adjacent matrix.

5. The apparatus of claim 1, wherein said matrix further comprises a pair of arms extending in a direction away from an outer surface of said form portion.

6. The apparatus of claim 1, wherein said form portion has at least one interproximal section.

7. The apparatus of claim 1, wherein said form portion has an incisal section.

8. The apparatus of claim 1 wherein said form portion has a lingual section.

9. The apparatus of claim 1, wherein said at least one wing has an intermediate portion and a free end, said intermediate portion dimensioned to extend interproximally.

10. The apparatus of claim 9, wherein said intermediate portion is dimensioned to permit insertion of two wings interproximally adjacent teeth.

11. A method for restoring a surface of a tooth forming an anatomically contoured inner surface on a matrix, said method comprising the steps of:
   forming an anatomically contoured inner surface on a matrix;
   positioning said anatomically contoured inner surface adjacent said surface of said tooth;
   adding restorative material between said inner surface and at least one desired surface of said tooth;
   pulling said inner surface against said restorative material;
   curing said restorative material; and removing said matrix from said tooth.

12. The method of claim 11 further comprising the step of affixing a pair of wings of said matrix together to secure said matrix to said teeth.

13. The method of claim 11 further comprising the step of extruding excess restorative material incisially from said matrix.

* * * * *